United States Patent
Matsuura et al.

(10) Patent No.: US 11,607,370 B2
(45) Date of Patent: Mar. 21, 2023

(54) DENTAL COMPOSITION

(71) Applicant: KURARAY NORITAKE DENTAL INC., Kurashiki (JP)

(72) Inventors: Ryo Matsuura, Niigata (JP); Yamato Nojiri, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 352 days.

(21) Appl. No.: 16/757,929

(22) PCT Filed: Oct. 22, 2018

(86) PCT No.: PCT/JP2018/039229
§ 371 (c)(1),
(2) Date: Apr. 21, 2020

(87) PCT Pub. No.: WO2019/082855
PCT Pub. Date: May 2, 2019

(65) Prior Publication Data
US 2021/0186823 A1    Jun. 24, 2021

(30) Foreign Application Priority Data
Oct. 23, 2017  (JP) ............................. JP2017-204537

(51) Int. Cl.
| A61K 6/896 | (2020.01) |
| A61K 6/30 | (2020.01) |
| A61K 6/40 | (2020.01) |
| A61K 6/62 | (2020.01) |

(52) U.S. Cl.
CPC .............. *A61K 6/896* (2020.01); *A61K 6/30* (2020.01); *A61K 6/40* (2020.01); *A61K 6/62* (2020.01)

(58) Field of Classification Search
CPC .................................................. A61K 6/896
See application file for complete search history.

(56) References Cited

U.S. PATENT DOCUMENTS

| 4,719,297 A | 1/1988 | Henne et al. |
| 2009/0299006 A1 | 12/2009 | Shinno et al. |
| 2010/0069524 A1 | 3/2010 | Tanaka et al. |
| 2010/0240796 A1 | 9/2010 | Bock et al. |
| 2011/0112209 A1 | 5/2011 | Tanaka et al. |
| 2016/0022549 A1 | 1/2016 | Catel et al. |

FOREIGN PATENT DOCUMENTS

| EP | 0 009 348 B1 | 7/1983 |
| EP | 1 849 449 A1 | 10/2007 |
| EP | 2 036 532 A2 | 3/2009 |
| EP | 3 624 753 A1 | 3/2020 |
| JP | 57-197289 A | 12/1982 |
| JP | 7-277913 A | 10/1995 |
| JP | 2008-1624 A | 1/2008 |
| JP | 2010-215624 A | 9/2010 |
| JP | 2016-513627 A | 5/2016 |
| WO | WO 2008/053990 A1 | 5/2008 |

OTHER PUBLICATIONS

International Search Report dated Jan. 8, 2019 in PCT/JP2018/039229 filed Oct. 22, 2018, 2 pages.
Taira et al., "Effects of primer containing silane and thiophosphate monomers on bonding resin to a leucite-reinforced ceramic," Journal of Dentistry, vol. 40, No. 5, 2012, pp. 353-358.
Sakai et al., "Silane primers rather than heat treatment contribute to adhesive bonding between tri-n-butylborane resin and a machinable leucite-reinforced ceramic," Dental Materials Journal, vol. 30, No. 6, 2011, pp. 854-860.
Extended European Search Report dated Jun. 21, 2021 in corresponding European Patent Application No. 18871636.9, 7 pages.

*Primary Examiner* — Benjamin J Packard
(74) *Attorney, Agent, or Firm* — Oblon, McClelland, Maier & Neustadt, L.L.P.

(57) ABSTRACT

The present invention provides a dental composition that exhibits high adhesive property for both dental restoration materials, such as porcelain, and tooth structure. The present invention relates to a one-part dental composition comprising a compound (A) represented by the following general formula (1), a monomer (B) having an acidic group, and water (C), $$Y-SiR_nX_{(3-n)} \quad (1),$$

wherein Y represents a monovalent organic group having a polymerizable group, R represents a group selected from the group consisting of an alkyl group, an aryl group, and an aralkyl group, X represents a hydroxyl group or a hydrolyzable group, and n represents an integer of 1 or 2, in which the plurality of R may be the same or different, and the plurality of X may be the same or different, and the content of the water (C) 1.0 to 50 mass %.

12 Claims, No Drawings

DENTAL COMPOSITION

TECHNICAL FIELD

The present invention relates to a dental composition, and to an adhesive and a primer comprising same.

BACKGROUND ART

In dental restorations, there has been increasing demand not just for functionality but for aesthetics after dental restoration. To meet such demands, ceramic materials such as composite resin, zirconia, alumina, lithium disilicate glass, and porcelain have come to be used as dental restoration materials for crown restoration, in addition to the conventional metals. Dental primers and adhesives are used for bonding of such dental restoration materials to adherends.

A dental adhesive composition containing a specific silane coupling agent and a specific phosphoric acid monoester is a known example of a primer and an adhesive (see Patent Literature 1). In the dental adhesive composition of Patent Literature 1, the silane coupling agent and the phosphoric acid monoester are provided as separate packages, and these are mixed immediately before use. However, use of a two-part adhesive composition, prepared as two separate packages of different components, involves complexity.

One-part adhesive compositions are known that aim at solving this issue. For example, Patent Literature 2 describes a specific one-part dental primer that contains a silane coupling agent, an acidic group-containing polymerizable monomer, and a volatile organic solvent. Patent Literature 3 describes a one-part adhesive composition containing a specific silane coupling agent, an acidic group-containing polymerizable monomer, a primary alcohol, and water, and in which the water content is 0.005 to 0.5 mass %.

CITATION LIST

Patent Literature

Patent Literature 1: JP 7(1995)-277913 A
Patent Literature 2: WO 2008/053990 A1
Patent Literature 3: JP 2008-1624 A

SUMMARY OF INVENTION

Technical Problem

Recent years have seen dental compositions being used for a range of different purposes, and this has created a demand for a one-part dental composition that can be used by itself for a variety of adherends, including teeth. However, because dental restoration materials such as porcelain greatly differ in property from the material of teeth, it is difficult to impart high adhesive property to both of these materials, and, in view of adhesive property, further improvements are needed for compositions of related art, including those described in Patent Literatures 2 and 3. One possible way of improving adhesive property for tooth structure is to mix water. However, simply mixing water seriously impairs the storage stability of silane coupling agent, and the adhesive property for dental restoration materials decreases as a result.

It is accordingly an object of the present invention to provide a dental composition that exhibits high adhesive property for both dental restoration materials, such as porcelain, and tooth structure. Another object of the present invention is to provide an adhesive and a primer comprising such a dental composition.

Solution to Problem

The present inventors conducted intensive studies to find a solution to the foregoing problem, and found that a dental composition that exhibits high adhesive property for both dental restoration materials, such as porcelain, and tooth structure can be provided by using a silane coupling agent having a specific structure, and by confining the water content of the composition within a specific range. The present invention was completed after further studies on the basis of this finding.

Specifically, the present invention relates to the following [1] to [13].

[1] A one-part dental composition comprising a compound (A) represented by the following general formula (1), a monomer (B) having an acidic group, and water (C), $$Y\text{-}SiR_nX_{(3-n)} \qquad (1),$$

wherein Y represents a monovalent organic group having a polymerizable group, R represents a group selected from the group consisting of an alkyl group, an aryl group, and an aralkyl group, X represents a hydroxyl group or a hydrolyzable group, and n represents an integer of 1 or 2, in which the plurality of R may be the same or different, and the plurality of X may be the same or different, and the content of the water (C) 1.0 to 50 mass %.

[2] The dental composition according to [1], wherein the polymerizable group is a (meth)acryloyl group.

[3] The dental composition according to [1] or [2], wherein the dental composition comprises the compound (A) in an amount of 0.1 to 50 mass %.

[4] The dental composition according to any one of [1] to [3], wherein the monomer (B) having an acidic group is a monomer having a phosphoric acid group.

[5] The dental composition according to any one of [1] to [4], further comprising a monomer (D) having no acidic group.

[6] The dental composition according to any one of [1] to [5], wherein the total content of all monomers contained in the dental composition is 20 to 90 mass %.

[7] The dental composition according to any one of [1] to [6], wherein the content of the monomer (B) having an acidic group is 1 to 50 mass % relative to all monomers contained in the dental composition.

[8] The dental composition according to any one of [1] to [7], further comprising a polymerization initiator (E).

[9] The dental composition according to [8], wherein the polymerization initiator (E) is a photopolymerization initiator (E-1).

[10] The dental composition according to any one of [1] to [9], wherein the dental composition has a pH of 1.5 to 4.0.

[11] The dental composition according to any one of [1] to [10], wherein the dental composition is packed in a container.

[12] An adhesive comprising the dental composition of any one of [1] to [11].

[13] A primer comprising the dental composition of any one of [1] to [11].

Advantageous Effects of Invention

The present invention provides a dental composition that exhibits high adhesive property for both dental restoration materials, such as porcelain, and tooth structure. An adhesive and a primer comprising such a dental composition are also provided.

DESCRIPTION OF EMBODIMENTS

The following describes the present invention in detail. In this specification, the upper limits and lower limits of numeric ranges (ranges of, for example, contents of components, values calculated from components, and values of physical properties) can be combined appropriately.

A dental composition of the present invention is a one-part dental composition comprising a compound (A) represented by the following general formula (1), a monomer (B) having an acidic group, and water (C), $$Y\text{-SiR}_n X_{(3-n)} \quad (1),$$

wherein Y represents a monovalent organic group having a polymerizable group, R represents a group selected from the group consisting of an alkyl group, an aryl group, and an aralkyl group, X represents a hydroxyl group or a hydrolyzable group, and n represents an integer of 1 or 2, in which the plurality of R may be the same or different, and the plurality of X may be the same or different, and the content of the water (C) 1.0 to 50 mass %. In this way, the dental composition can exhibit high adhesive property for both dental restoration materials, such as porcelain, and tooth structure.

Although the reason that a configuration of the present invention produces the foregoing desirable effect remains somewhat unclear, one possible explanation is that the compound (A), by containing at least one R, is less likely to undergo self-condensation reaction than traditional silane coupling agents used in dentistry, and produces a condensation product having smaller steric hinderance, allowing X from compound (A) to more easily bind to a dental restoration material.

Compound (A)

Compound (A) is represented by general formula (1): $Y\text{-SiR}_n X_{(3-n)}$, wherein Y represents a monovalent organic group having a polymerizable group, R represents a group selected from the group consisting of an alkyl group, an aryl group, and an aralkyl group, X represents a hydroxyl group or a hydrolyzable group, and n represents an integer of 1 or 2, in which the plurality of R may be the same or different, and the plurality of X may be the same or different.

The polymerizable group of Y is not limited to particular kinds of polymerizable groups, and may be, for example, a (meth)acryloyl group, a vinyl group, a mercapto group, or an epoxy group. For advantages such as further improvement of adhesive property for both dental restoration materials and tooth structure, the polymerizable group is preferably a (meth)acryloyl group, more preferably a methacryloyl group. The polymerizable group may be bound to the monovalent organic group either directly or via a divalent group having a heteroatom such as an oxygen atom or a nitrogen atom. That is, the (meth)acryloyl group may form a (meth)acryloyloxy group or a (meth)acrylamide group.

The polymerizable group of Y is not limited to particular numbers, and Y has preferably one to four polymerizable groups, more preferably one or two polymerizable groups, even more preferably one polymerizable group. When Y has a plurality of polymerizable groups, the polymerizable groups may be the same or different.

Y may be formed solely from the polymerizable group, or may be formed by the functional group and the organic group being bonded to each other either directly or indirectly via a divalent group having a heteroatom such as an oxygen atom or a nitrogen atom. The organic group is not particularly limited, and may be, for example, an alkyl group having 1 to 20 carbon atoms, an aryl group having 6 to 18 carbon atoms, or an aralkyl group having 7 to 26 carbon atoms. For advantages such as further improvement of adhesive property for both dental restoration materials and tooth structure, the organic group is preferably an alkyl group having 1 to 20 carbon atoms, more preferably an alkyl group having 1 to 12 carbon atoms, even more preferably an alkyl group having 1 to 5 carbon atoms. Examples of the alkyl group having 1 to 5 carbon atoms include a methyl group, an ethyl group, an n-propyl group, an isopropyl group, an n-butyl group, and an n-pentyl group. Preferred are a methyl group and an n-propyl group. More preferred is an n-propyl group.

Specific examples of Y include a (meth)acryloyloxymethyl group, a γ-(meth)acryloyloxypropyl group, a γ-(meth)acrylamidepropyl group, a vinyl group, a (meth)allyl group, and a γ-glycidoxypropyl group. Preferred are a (meth)acryloyloxymethyl group and a γ-(meth)acryloyloxypropyl group. More preferred is a γ-(meth)acryloyloxypropyl group.

The alkyl group represented by R is not limited to particular kinds of alkyl groups, and may be, for example, an alkyl group having 1 to 5 carbon atoms. Specific examples include a methyl group, an ethyl group, an n-propyl group, an isopropyl group, an n-butyl group, and an n-pentyl group.

The aryl group represented by R is not limited to particular kinds of aryl groups, and may be, for example, an aryl group having 6 to 10 carbon atoms. Specific examples include a phenyl group and a naphthyl group.

The aralkyl group represented by R is not limited to particular kinds of aralkyl groups, and may be, for example, an aralkyl group having 7 to 12 carbon atoms. Specific examples include a benzyl group.

For advantages such as further improvement of adhesive property for both dental restoration materials and tooth structure, R is preferably an alkyl group, more preferably an alkyl group having 1 to 5 carbon atoms, even more preferably a methyl group.

The hydrolyzable group represented by X may be a group that is capable of undergoing hydrolysis to form a silanol group with the silicon atom attached thereto. Examples include an alkoxy group, an acyloxy group, a siloxy group, and a halogen atom.

The alkoxy group is not limited to particular kinds of alkoxy groups, and may be, for example, an alkoxy group having 1 to 5 carbon atoms. Specific examples include a methoxy group, an ethoxy group, an n-propoxy group, an isopropoxy group, an n-butoxy group, and an n-pentyloxy group.

The acyloxy group is not limited to particular kinds of acyloxy groups, and may be, for example, an acyloxy group having 1 to 5 carbon atoms. Specific examples include a formyloxy group, an acetoxy group, an n-propionyloxy group, an isopropionyloxy group, an n-butanoyloxy group, and an n-pentanoyloxy group.

The siloxy group is not limited to particular kinds of siloxy groups, and may be, for example, a trimethylsiloxy group.

The halogen atom is not limited to particular kinds of halogen atoms, and may be, for example, a chlorine atom or a bromine atom.

For advantages such as further improvement of adhesive property for both dental restoration materials and tooth structure, X is preferably an alkoxy group, more preferably an alkoxy group having 1 to 5 carbon atoms, even more preferably a methoxy group or an ethoxy group.

The symbol n represents an integer of 1 or 2. For advantages such as further improvement of adhesive property for both dental restoration materials and tooth structure, n is preferably 1. When n is 1, the plurality of X may be the same or different. When n is 2, the plurality of R may be the same or different.

Specific examples of compound (A) include 3-(meth)acryloyloxypropylmethyldimethoxysilane, 3-(meth)acryloyloxypropylmethyldiethoxysilane, 3-(meth)acryloyloxypropylmethyldiisopropoxysilane, 3-(meth)acryloyloxypropylmethylditrimethylsiloxysilane, 3-(meth)acryloyloxypropylmethyldihexyloxysilane, (meth)acryloyloxy-2-(2-vinyloxyethoxy)ethylmethyldimethoxysilane, 6-(meth)acryloyloxyhexylmethyldimethoxysilane, (meth)acryloyloxy-p-phenylethylmethyldimethoxysilane, 6-(meth)acryloyloxyhexylmethyldiethoxysilane, 10-(meth)acryloyloxydecylmethyldimethoxysilane, 11-(meth)acryloyloxyundecylmethyldimethoxysilane, 11-(meth)acryloyloxyundecylmethyldiethoxysilane, 11-(meth)acryloyloxyundecylmethyldihexyloxysilane, 20-(meth)acryloyloxyeicosylmethyldimethoxysilane, 3-(meth)acryloyloxypropylphenyldimethoxysilane, 3-(meth)acryloyloxypropylmethyldichlorosilane, 11-(meth)acryloyloxyundecylmethyldichlorosilane, 11-(meth)acryloyloxyundecylethyldichlorosilane, vinylmethyldimethoxysilane, vinylmethyldiethoxysilane, vinylmethyldichlorosilane, vinylmethyldiacetoxysilane, vinylmethyldi(2-methoxyethoxy)silane, 3-glycidoxypropylmethyldimethoxysilane, 3-glycidoxypropylmethyldiethoxysilane, allylmethyldiethoxysilane, 3-(meth)acryloyloxypropyldimethylmonomethoxysilane, 3-(meth)acryloyloxypropyldimethylmonoethoxysilane, 3-(meth)acryloyloxypropyldimethylmonoisopropoxysilane, 3-(meth)acryloyloxypropyldimethylmonotrimethylsiloxysilane, 3-(meth)acryloyloxypropyldimethylmonohexyloxysilane, (meth)acryloyloxy-2-(2-vinyloxyethoxy)ethyldimethylmonomethoxysilane, 6-(meth)acryloyloxyhexyldimethylmonomethoxysilane, (meth)acryloyloxy-p-phenylethyldimethylmonomethoxysilane, 6-(meth)acryloyloxyhexyldimethylmonoethoxysilane, 10-(meth)acryloyloxydecyldimethylmonomethoxysilane, 11-(meth)acryloyloxyundecyldimethylmonomethoxysilane, 11-(meth)acryloyloxyundecyldimethylmonoethoxysilane, 11-(meth)acryloyloxyundecyldimethylmonohexyloxysilane, 20-(meth)acryloyloxyeicosyldimethylmonomethoxysilane, 3-(meth)acryloyloxypropyldiphenylmonomethoxysilane, 3-(meth)acryloyloxypropyldimethylmonochlorosilane, 11-(meth)acryloyloxyundecyldimethylmonochlorosilane, 11-(meth)acryloyloxyundecyldiethylmonochlorosilane, vinyldimethylmonomethoxysilane, vinyldimethylmonoethoxysilane, vinyldimethylmonochlorosilane, vinyldimethylmonoacetoxysilane, vinyldimethylmono(2-methoxyethoxy)silane, 3-glycidoxypropyldimethylmonomethoxysilane, 3-glycidoxypropyldimethylmonoethoxysilane, and allyldimethylmonoethoxysilane. Compound (A) may be a hydrolysis and/or a condensation product of these. Compound (A) may be used alone, or two or more thereof may be used in combination. In view of desirable adhesive property and desirable ease of handling, preferred are 3-(meth)acryloyloxypropylmethyldimethoxysilane, 3-(meth)acryloyloxypropylmethyldiethoxysilane, 3-(meth)acryloyloxypropyldimethylmonomethoxysilane, and hydrolysates of these.

For advantages such as further improvement of adhesive property for both dental restoration materials and tooth structure, the content of the compound (A) in a dental composition of the present invention is preferably 0.1 mass % or more, more preferably 1 mass % or more, even more preferably 3 mass % or more, and is preferably 50 mass % or less, more preferably 30 mass % or less, even more preferably 20 mass % or less, particularly preferably 15 mass % or less. Despite the possible hydrolysis and/or condensation of the compound (A) in the dental composition, the foregoing contents assume that the compound (A) is not hydrolyzed and/or condensed.

Monomer (B) Having Acidic Group

Monomer (B) having an acidic group penetrates and binds to tooth structure through demineralization, improving adhesive property for tooth structure. Monomer (B) having an acidic group may be a monomer having at least one acidic group such as a phosphoric acid group, a phosphonic acid group, a pyrophosphoric acid group, a carboxylic acid group, and a sulfonic acid group, and at least one polymerizable group such as an acryloyl group, a methacryloyl group, an acrylamide group, and a methacrylamide group. In view of adhesive property for enamel, the monomer (B) having an acidic group is preferably a monofunctional monomer having any one of an acryloyl group, a methacryloyl group, an acrylamide group, and a methacrylamide group. Specific examples include the following.

Examples of the monomer having a phosphoric acid group include:

phosphoric acid group-containing monofunctional (meth)acrylate compounds such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, 2-(meth)acryloyloxyethylphenyl hydrogen phosphate, 2-(meth)acryloyloxyethyl-2-bromoethyl hydrogen phosphate, 2-(meth)acryloyloxyethyl-(4-methoxyphenyl)hydrogen phosphate, and 2-(meth)acryloyloxypropyl-(4-methoxyphenyl)hydrogen phosphate, and acid chlorides, alkali metal salts, and ammonium salts thereof;

phosphoric acid group-containing bifunctional(meth)acrylate compounds such as bis[2-(meth)acryloyloxyethyl] hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, and 1,3-di(meth)acryloyloxypropyl dihydrogen phosphate, and acid chlorides, alkali metal salts, and ammonium salts thereof.

Examples of the monomer having a phosphonic acid group include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexylphosphonoacetate, and 10-(meth)acryloyloxydecylphosphonoacetate, and acid chlorides, alkali metal salts, and ammonium salts thereof.

Examples of the monomer having a pyrophosphoric acid group include bis[2-(meth)acryloyloxyethyl]pyrophosphate, bis[4-(meth)acryloyloxybutyl]pyrophosphate, bis[6-(meth)

acryloyloxyhexyl]pyrophosphate, bis[8-(meth)acryloyloxyoctyl]pyrophosphate, and bis[10-(meth)acryloyloxydecyl]pyrophosphate, and acid chlorides, alkali metal salts, and ammonium salts thereof.

Examples of the monomer having a carboxylic acid group include (meth)acrylic acid, 4-(meth)acryloyloxyethoxycarbonylphthalic acid, 4-(meth)acryloyloxyethyltrimellitic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, and 5-(meth)acryloylaminopentylcarboxylic acid, and acid anhydrides, acid chlorides, alkali metal salts, and ammonium salts thereof.

Examples of the monomer having a sulfonic acid group include 2-(meth)acrylamide-2-methylpropanesulfonic acid, and 2-sulfoethyl(meth)acrylate, and acid chlorides, alkali metal salts, and ammonium salts thereof.

In view of developing even more desirable adhesive property for tooth structure, the monomer (B) having an acidic group is preferably a monomer having a phosphoric acid group, or a monomer having a pyrophosphoric acid group, more preferably a monomer having a phosphoric acid group, even more preferably a monofunctional monomer having a phosphoric acid group. Of these monomers, preferred is a phosphoric acid group-containing (meth)acrylate monofunctional monomer having a $C_6$ to $C_{20}$ alkyl or alkylene group as a main chain within the molecule. More preferred is a phosphoric acid group-containing (meth)acrylate monofunctional monomer having a $C_8$ to $C_{12}$ alkylene group as a main chain within the molecule (e.g., 10-methacryloyloxydecyl dihydrogen phosphate). The monomer (B) having an acidic group may be used alone, or two or more thereof may be used in combination.

For advantages such as further improvement of adhesive property for both dental restoration materials and tooth structure, the content of the monomer (B) having an acidic group in a dental composition of the present invention is preferably 1 mass % or more, more preferably 3 mass % or more, and is preferably 50 mass % or less, more preferably 30 mass % or less, even more preferably 20 mass % or less based on the mass of the all monomers contained in the dental composition. In this specification, typical examples of "all monomers contained in the dental composition" include radical polymerizable monomers such as (meth)acryloyl group-containing monomers, and all the other monomers contained in the dental composition and that do not classify as compound (A).

Water (C)

With the specific amount of water (C) contained in a dental composition of the present invention, it is possible to promote the demineralization effect of the monomer (B) having an acidic group. In view of preventing entry of impurities harmful to adhesive property, the water used to prepare a dental composition of the present invention is preferably distilled water or ion-exchange water.

In order to produce a dental composition having high adhesive property for both dental restoration materials, such as porcelain, and tooth structure, the content of water (C) in a dental composition of the present invention needs to be 1.0 mass % or more. Preferably, the water content is 5.0 mass % or more, more preferably 10 mass % or more. The content of water (C) needs to be 50 mass % or less, and is preferably 30 mass % or less, more preferably 20 mass % or less, because an excessively high content of water (C) may result in decrease of adhesive property.

Monomer (D) Having No Acidic Group

In view of adhesive property, the dental composition of the present invention preferably further comprises a monomer (D) having no acidic group. The monomer (D) having no acidic group may be a known monomer having no acidic group. Examples include a hydrophobic monomer (D-1) having no acidic group, and a hydrophilic monomer (D-2) having no acidic group. The monomer (D) having no acidic group may be used alone, or two or more thereof may be used in combination. For example, the hydrophobic monomer (D-1) having no acidic group and the hydrophilic monomer (D-2) having no acidic group may be used in combination.

(i) Hydrophobic Monomer (D-1) Having No Acidic Group

With a dental composition of the present invention containing the hydrophobic monomer (D-1) having no acidic group, it is possible to improve the mechanical strength, ease of handling, and other properties of a cured product (a cured product of the dental composition). The hydrophobic monomer (D-1) having no acidic group is preferably a polymerizable group-containing radical polymerizable monomer having no acidic group. For advantages such as ease of radical polymerization, the polymerizable group is preferably a (meth)acryloyl group or a (meth)acrylamide group. The hydrophobic monomer (D-1) having no acidic group may be one having a solubility of less than 10 mass % for water at 25° C. Examples of such monomers include cross-linkable monomers such as aromatic bifunctional monomers, aliphatic bifunctional monomers, and tri- and higher-functional monomers.

Examples of the aromatic bifunctional monomers include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane.

Preferred are 2,2-bis[4-(3-methacryloyloxy-2-hydroxypropoxy)phenyl]propane (commonly known as "Bis-GMA"), 2,2-bis(4-(meth)acryloyloxyethoxyphenyl)propane, and 2,2-bis(4-methacryloyloxypolyethoxyphenyl)propane (the average number of moles of ethoxy group added is 2.6; commonly known as "D-2.6E"), 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, and 2,2-bis(4-(meth)acryloyloxypentaethoxyphenyl)propane. More preferred are 2,2-bis[4-(3-methacryloyloxy-2-hydroxypropoxy)phenyl]propane (commonly known as "Bis-GMA"), and 2,2-bis(4-methacryloyloxypolyethoxyphenyl)propane (the average number of moles of ethoxy group added is 2.6; commonly known as "D-2.6E").

Examples of the aliphatic bifunctional monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth) acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl)di(meth)acrylate, N-methacryloyloxyethylacrylamide, N-methacryloyloxypropylacrylamide, N-methacryloyloxybutylacrylamide, N-(1-ethyl-(2-methacryloyloxy)ethyl)acrylamide, and N-(2-(2-methacryloyloxyethoxy)ethyl)acrylamide.

Preferred are glycerol di(meth)acrylate, triethylene glycol diacrylate, triethylene glycol dimethacrylate (commonly known as "3G"), neopentyl glycol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl)dimethacrylate (commonly known as "UDMA"), N-methacryloyloxyethylacrylamide (commonly known as "MAEA"), and N-methacryloyloxypropylacrylamide.

Examples of the tri- and higher-functional monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetra(meth)acrylate, and 1,7-diacryloyloxy-2,2,6,6-tetra(meth)acryloyloxymethyl-4-oxyheptane.

Preferred is N, N-(2,2,4-trimethylhexamethylene)bis[2-(aminocarboxy)propane-1,3-diol]tetramethacrylate.

In view of the mechanical strength and ease of handling of a cured product, preferred as the hydrophobic monomer (D-1) having no acidic group are aromatic bifunctional monomers and aliphatic bifunctional monomers. Bis-GMA, D-2.6E, 3G, UDMA, and MAEA are more preferred, and Bis-GMA, 3G, UDMA, and MAEA are even more preferred in view of bond strength and the mechanical strength of a cured product. The hydrophobic monomer (D-1) having no acidic group may be used alone, or two or more thereof may be used in combination.

In view of advantages such as improved penetrability into tooth structure and improved bond strength, the content of the hydrophobic monomer (D-1) having no acidic group in a dental composition of the present invention is preferably 9 mass % or more, more preferably 15 mass % or more, even more preferably 20 mass % or more, particularly preferably 30 mass % or more, and is preferably 90 mass % or less, more preferably 80 mass % or less, even more preferably 75 mass % or less, particularly preferably 70 mass % or less based on the mass of the all monomers contained in the dental composition.

(ii) Hydrophilic Monomer (D-2) Having No Acidic Group

With a dental composition of the present invention containing the hydrophilic monomer (D-2) having no acidic group, it is possible to promote penetration of the components of the dental composition into tooth structure. The hydrophilic monomer (D-2) having no acidic group itself is also able to penetrate into tooth structure, and bind to the organic components (e.g., collagen) of the tooth structure. The hydrophilic monomer (D-2) having no acidic group is preferably a polymerizable group-containing radical polymerizable monomer having no acidic group. For advantages such as ease of radical polymerization, the polymerizable group is preferably a (meth)acryloyl group or a (meth) acrylamide group. The hydrophilic monomer (D-2) having no acidic group may be one having a solubility of 10 mass % or more for water at 25° C., preferably one having a solubility of 30 mass % or more for water at 25° C., more preferably one that can dissolve in water at 25° C. in any proportions.

The hydrophilic monomer (D-2) having no acidic group is preferably one having a hydrophilic group such as a hydroxyl group, an oxymethylene group, an oxyethylene group, an oxypropylene group, or an amide group. Examples include (meth)acrylates such as 2-hydroxyethyl(meth)acrylate, 3-hydroxypropyl(meth)acrylate, 2-hydroxypropyl(meth)acrylate, 1,3-dihydroxypropyl(meth)acrylate, 2,3-dihydroxypropyl(meth)acrylate, 2-trimethylammoniumethyl(meth)acrylchloride, and polyethylene glycol di(meth)acrylate (having at least nine oxyethylene groups); and monofunctional (meth)acrylamides such as N-methylol(meth)acrylamide, N-hydroxyethyl(meth)acrylamide, N-methoxymethyl(meth)acrylamide, N-ethoxymethyl(meth)acrylamide, diacetone(meth)acrylamide, 4-(meth)acryloylmorpholine, and disubstituted (meth)acrylamides represented by the following general formula (2).

[Chem. 1]

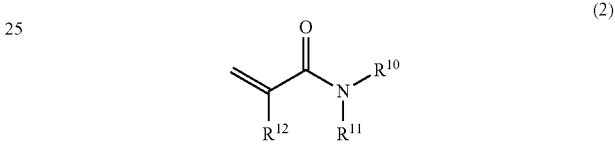

In the general formula (2), $R^{10}$ and $R^{11}$ each independently represent an optionally substituted linear or branched alkyl group having 1 to 3 carbon atoms, and $R^{12}$ is a hydrogen atom or a methyl group.

Examples of the $C_1$ to $C_3$ alkyl group represented by $R^{10}$ and $R^{11}$ include a methyl group, an ethyl group, an n-propyl group, and an isopropyl group. Examples of the optional substituents of the $C_1$ to $C_3$ alkyl include a hydroxyl group.

Examples of the disubstituted (meth)acrylamides represented by the general formula (2) include N,N-dimethyl(meth)acrylamide, N,N-diethyl(meth)acrylamide, and N,N-di(hydroxyethyl)(meth)acrylamide. In view of properties such as storage stability, N,N-dimethylacrylamide and N,N-diethylacrylamide are preferred, and N,N-diethylacrylamide is more preferred.

In view of adhesive property for tooth structure, the hydrophilic monomer (D-2) having no acidic group is preferably 2-hydroxyethyl(meth)acrylate, 2,3-dihydroxypropyl(meth)acrylate, or a monofunctional (meth)acrylamide, more preferably 2-hydroxyethyl(meth)acrylate, 2,3-dihydroxypropyl(meth)acrylate, diacetone(meth)acrylamide, or a disubstituted (meth)acrylamide represented by the general formula (2), even more preferably 2-hydroxyethyl(meth)acrylate or a disubstituted (meth)acrylamide represented by the general formula (2), particularly preferably 2-hydroxyethyl methacrylate or N,N-diethylacrylamide. The hydrophilic monomer (D-2) having no acidic group may be used alone, or two or more thereof may be used in combination.

In view of advantages such as improved bond strength, the content of the hydrophilic monomer (D-2) having no acidic group in a dental composition of the present invention is preferably 9 mass % or more, more preferably 15 mass % or more, even more preferably 20 mass % or more, particularly preferably 30 mass % or more, and is preferably 90 mass % or less, more preferably 80 mass % or less, even more preferably 75 mass % or less, particularly preferably 70 mass % or less based on the mass of the all monomers contained in the dental composition.

For advantages such as further improvement of adhesive property for both dental restoration materials and tooth structure, the total content of all monomers contained in a dental composition of the present invention, including the monomer (B) having an acidic group, and the optional monomers having no acidic group, is preferably 20 mass % or more, more preferably 35 mass % or more, and is preferably 90 mass % or less, more preferably 80 mass % or less.

Polymerization Initiator (E)

In view of adhesive property, the dental composition of the present invention preferably further comprises a polymerization initiator (E). The polymerization initiator (E) may be a known polymerization initiator. For example, a photopolymerization initiator (E-1) and a chemical polymerization initiator (E-2) may be used. The polymerization initiator (E) may be used alone, or two or more thereof may be used in combination. For example, the photopolymerization initiator (E-1) and the chemical polymerization initiator (E-2) may be used in combination.

(i) Photopolymerization Initiator (E-1)

Examples of the photopolymerization initiator (E-1) include (bis)acylphosphine oxides (including salts), thioxanthones (including salts such as quaternary ammonium salts), ketals, α-diketones, coumarins, anthraquinones, benzoin alkyl ether compounds, and α-aminoketone compounds.

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di(2,6-dimethylphenyl)phosphonate.

Examples of bisacylphosphine oxides in the (bis) acylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl) phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis (2,3,6-trimethylbenzoyl)-2,4,4-trimethylpentylphosphine oxide.

The acylphosphine oxides may be water-soluble acylphosphine oxides. Examples of the water-soluble acylphosphine oxides include acylphosphine oxides having, for example, alkali metal ions, alkali earth metal ions, pyridinium ions, or ammonium ions within the molecule. The water-soluble acylphosphine oxides can be synthesized by using a method disclosed in, for example, European Patent No. 0009348 or JP 57 (1982)-197289A.

Specific examples of the water-soluble acylphosphine oxides include sodium monomethyl acetylphosphonate, sodium monomethyl(1-oxopropyl)phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium methyl 4-(hydroxymethoxyphosphinyl)-4-oxobutanoate, monosodium methyl 4-oxo-4-phosphonobutanoate, sodium acetylphenylphosphinate, sodium (1-oxopropyl)pentylphosphinate, sodium methyl 4-(hydroxypentylphosphinyl)-4-oxobutanoate, sodium acetylpentylphosphinate, sodium acetylethylphosphinate, lithium methyl 4-(hydroxymethylphosphinyl)-4-oxobutanoate, dilithium 4-(hydroxymethylphosphinyl)-4-oxobutanoate, sodium acetylphosphinate, sodium acetylmethylphosphinate oxime, sodium acetylmethylphosphinate-O-benzyloxime, sodium acetylmethylphosphinate semicarbazone, sodium formylmethylphosphinate, sodium methyl(1-oxopropyl)phosphinate, sodium acetylmethylphosphinate thiosemicarbazone, sodium salts of 2,4,6-trimethylbenzoylphenylphosphine oxide, potassium salts of 2,4,6-trimethylbenzoylphenylphosphine oxide, and ammonium salts of 2,4,6-trimethylbenzoylphenylphosphine oxide.

Particularly preferred among these (bis)acylphosphine oxides are sodium salts of 2,4,6-trimethylbenzoyldiphenylphosphine oxide, 2,4,6-trimethyl benzoylmethoxyphenylphosphine oxide, bis(2,4,6-trimethylbenzoyl)phenylphosphine oxide, and 2,4,6-trimethylbenzoylphenylphosphine oxide.

Examples of the thioxanthones include thioxanthone, 2-chlorothioxanthen-9-one, 2-hydroxy-3-(9-oxy-9H-thioxanthen-4-yloxy)-N,N,N-trimethylpropaneaminium chloride, 2-hydroxy-3-(1-methyl-9-oxo-9H-thioxanthen-4-yloxy)-N,N,N-trimethyl-1-propaneaminium chloride, 2-hydroxy-3-(9-oxo-9H-thioxanthen-2-yloxy)-N,N,N-trimethyl-1-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

Preferred among these thioxanthones are 2-chlorothioxanthen-9-one, and 2-hydroxy-3-(3,4-dimethyl-9H-thioxanthen-2-yloxy)-N,N,N-trimethyl-1-propaneaminium chloride.

Examples of the ketals include benzyl dimethyl ketal, and benzyl diethyl ketal.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Particularly preferred is camphorquinone for its maximum absorption wavelength occurring in the visible light region.

Examples of the coumarins include 3,3'-carbonylbis(7-diethylaminocoumarin), 3-(4-methoxybenzoyl)coumarin, 3-thienylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl) coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f] coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f] coumarin, 3-benzoyl-6-nitrocoumarin, 3-benzoyl-7-diethylaminocoumarin, 7-dimethylamino-3-(4-methoxybenzoyl) coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f] coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrano[6,7,8-ij]quinolizin-11-one, and 10-(2-benzothiazoyl)-2,3,6,7-tetrahydro-1,1,7,7-tetramethyl-1H, 5H, 11H-[1]benzopyrrano[6,7,8-ij] quinolizin-11-one.

Preferred among these coumarins are 3,3'-carbonylbis(7-diethylaminocoumarin) and 3,3'-carbonylbis(7-dibutylaminocoumarin).

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ether compounds include benzoin methyl ether, benzoin ethyl ether, benzoin isopropyl ether, and benzoin isobutyl ether.

Examples of the α-aminoketone compounds include 2-methyl-1-[4-(methylthio)phenyl]-2-morpholinopropan-1-one.

The photopolymerization initiator (E-1) is preferably at least one selected from the group consisting of a (bis)acylphosphine oxide, an α-diketone, and a coumarin. In this way, a dental composition can be provided that has desirable photocurability both in the visible light region and the near ultraviolet region so that sufficient photocurability can be ensured regardless of whether the light source used is a halogen lamp, a light emitting diode (LED), or a xenon lamp.

(ii) Chemical Polymerization Initiator (E-2)

The chemical polymerization initiator (E-2) may be a known chemical polymerization initiator. Organic peroxides are particularly preferred. Examples of the organic peroxides include ketone peroxides, hydroperoxides, diacyl peroxides, dialkyl peroxides, peroxy ketals, peroxy esters, and peroxydicarbonates.

Examples of the ketone peroxides include methyl ethyl ketone peroxide, methyl isobutyl ketone peroxide, methyl cyclohexanone peroxide, and cyclohexanone peroxide.

Examples of the hydroperoxides include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxy ketals include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxy esters include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxyvalerate.

Examples of the peroxydicarbonates include di-3-methoxybutyl peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

From an overall balance of safety, storage stability, and radical generating potential, preferred among these organic peroxides are diacyl peroxides, particularly preferably benzoyl peroxide.

The polymerization initiator (E) is preferably a photopolymerization initiator (E-1).

In view of the adhesive property and other properties of the dental composition obtained, the content of polymerization initiator (E) in a dental composition of the present invention is preferably 0.01 mass % or more, more preferably 0.05 mass % or more, even more preferably 0.1 mass % or more, and is preferably 10 mass % or less.

Polymerization Accelerator (F)

The dental composition of the present invention may further comprise a polymerization accelerator (F). Preferably, the polymerization accelerator (F) is used with the polymerization initiator (E). The polymerization accelerator (F) may be a known polymerization accelerator. Examples include amines, sulfinic acids (including salts), borate compounds, derivatives of barbituric acid, triazine compounds, copper compounds, tin compounds, vanadium compounds, halogen compounds, aldehydes, thiol compounds, sulfites, bisulfites, and thiourea compounds. The polymerization accelerator (F) may be used alone, or two or more thereof may be used in combination.

The amines can be divided into aliphatic amines and aromatic amines. Examples of the aliphatic amines include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolaminedimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. In view of the adhesive property and storage stability of the dental composition, preferred are tertiary aliphatic amines, more preferably N-methyldiethanolamine and triethanolamine.

Examples of the aromatic amines include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N, N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-[(meth)acryloyloxy]ethyl 4-(N,N-dimethylamino)benzoate, 4-(N, N-dimethylamino)benzophenone, butyl 4-dimethylaminobenzoate, and 4-(dimethylamino)benzonitrile. In view of the ability to impart desirable adhesive property to the dental composition, preferred are N,N-bis(2-hydroxyethyl)-p-toluidine, ethyl 4-(N,N-dimethylamino)benzoate, n-butoxyethyl 4-(N,N-dimethylamino)benzoate, and 4-(N,N-dimethylamino)benzophenone.

Examples of the sulfinic acids include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Particularly preferred are sodium benzenesulfinate, sodium p-toluenesulfinate, and sodium 2,4,6-triisopropylbenzenesulfinate.

Preferred as the borate compounds are arylborate compounds. Examples of the arylborate compounds include borate compounds having 1 to 4 aryl groups per molecule.

Examples of the borate compounds having one aryl group per molecule include trialkylphenylboron, trialkyl(p-chlorophenyl)boron, trialkyl(p-fluorophenyl)boron, trialkyl[3,5-bis(trifluoromethyl)phenyl]boron, trialkyl[3,5-bis(1,1,1,3,3,3-hexafluoro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl (p-butyloxyphenyl)boron, trialkyl(m-butyloxyphenyl) boron, trialkyl(p-octyloxyphenyl)boron, trialkyl(m-octyloxyphenyl)boron (the alkyl group in these borate compounds is, for example, n-butyl, n-octyl, or n-dodecyl), and salts thereof (including sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having two aryl groups per molecule include dialkyldiphenylboron, dialkyldi(p-chlorophenyl)boron, dialkyldi(p-fluorophenyl)boron, dialkyldi[3,5-bis(trifluoromethyl)phenyl]boron, dialkyldi[3,5-bis(1,1,1,3,3,3-hexafluoro-2-methoxy-2-propyl) phenyl]boron, dialkyldi(p-nitrophenyl)boron, dialkyldi(m-nitrophenyl)boron, dialkyldi(p-butylphenyl)boron, dialkyldi (m-butylphenyl)boron, dialkyldi(p-butyloxyphenyl)boron, dialkyldi(m-butyloxyphenyl)boron, dialkyldi(p-octyloxyphenyl)boron, dialkyldi(m-octyloxyphenyl)boron (the alkyl group in these borate compounds is, for example, n-butyl, n-octyl, or n-dodecyl), and salts thereof (including sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having three aryl groups per molecule include monoalkyltriphenylboron, monoalkyltri(p-chlorophenyl)boron, monoalkyltri(p-fluorophenyl)boron, monoalkyltri[3,5-bis(trifluoromethyl)phenyl] boron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, monoalkyltri(m-octyloxyphenyl)boron (the alkyl group in these borate compounds is, for example, n-butyl, n-octyl, or n-dodecyl), and salts thereof (including sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

Examples of the borate compounds having four aryl groups per molecule include tetraphenylboron, tetrakis(p-chlorophenyl)boron, tetrakis(p-fluorophenyl)boron, tetrakis [3,5-bis(trifluoromethyl)phenyl]boron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-fluorophenyl)triphenylboron, [3,5-bis(trifluoromethyl)phenyl]triphenylboron, (p-nitrophenyl)triphenylboron, (m-butyloxyphenyl)triphenylboron, (p-butyloxyphenyl)triphenylboron, (m-octyloxyphenyl)triphenylboron, (p-octyloxyphenyl)triphenylboron, and salts thereof (including sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, and butylquinolinium salts).

In view of storage stability, preferred among these arylborate compounds are borate compounds having three or four aryl groups per molecule. The arylborate compound may be used alone, or two or more thereof may be used in combination.

Examples of the derivatives of barbituric acid include barbituric acid, 1,3-dimethyl barbituric acid, 1,3-diphenyl barbituric acid, 1,5-dimethyl barbituric acid, 5-butyl barbituric acid, 5-ethyl barbituric acid, 5-isopropyl barbituric acid, 5-cyclohexyl barbituric acid, 1,3,5-trimethyl barbituric acid, 1,3-dimethyl-5-ethyl barbituric acid, 1,3-dimethyl-5-n-butyl barbituric acid, 1,3-dimethyl-5-isobutyl barbituric acid, 1,3-dimethyl-5-cyclopentyl barbituric acid, 1,3-dimethyl-5-cyclohexyl barbituric acid, 1,3-dimethyl-5-phenyl barbituric acid, 1-cyclohexyl-1-ethyl barbituric acid, 1-benzyl-5-phenyl barbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid, thiobarbituric acids, and salts thereof. Examples of the salts of the derivatives of barbituric acid include alkali metal salts and alkali-earth metal salts, specifically, sodium 5-butyl barbiturate, sodium 1,3,5-trimethyl barbiturate, and sodium 1-cyclohexyl-5-ethyl barbiturate.

The derivatives of barbituric acid are particularly preferably 5-butyl barbituric acid, 1,3,5-trimethyl barbituric acid, 1-cyclohexyl-5-ethyl barbituric acid, 1-benzyl-5-phenyl barbituric acid, and sodium salts thereof.

Examples of the triazine compounds include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Preferred in view of polymerization activity is 2,4,6-tris(trichloromethyl)-s-triazine. Preferred in view of storage stability are 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine. The triazine compound may be used alone, or two or more thereof may be used in combination.

Examples of the copper compounds include copper acetylacetonate, copper(II) acetate, copper oleate, copper(II) chloride, and copper(II) bromide.

Examples of the tin compounds include di-n-butyltin dimaleate, di-n-octyltin dimaleate, di-n-octyltin dilaurate, and di-n-butyltin dilaurate. Preferred are di-n-octyltin dilaurate and di-n-butyltin dilaurate.

The vanadium compounds are preferably vanadium compounds having a valence of IV and V. Examples of vanadium compounds having a valence of IV and V include vanadium(IV) oxide, vanadium(IV)oxy acetylacetonate, vanadyl oxalate, vanadyl sulfate, vanadium(IV) oxobis(1-phenyl-1,3-butanedionate), bis(maltolato)oxovanadium(IV), vanadium(V) oxide, sodium metavanadate, and ammonium metavanadate.

Examples of the halogen compounds include dilauryldimethylammonium chloride, lauryldimethylbenzylammonium chloride, benzyltrimethylammonium chloride, tetramethylammonium chloride, benzyldimethylcetylammonium chloride, and dilauryldimethylammonium bromide.

Examples of the aldehydes include terephthalaldehyde, and derivatives of benzaldehyde. Examples of the derivatives of benzaldehyde include dimethylaminobenzaldehyde, p-methyloxybenzaldehyde, p-ethyloxybenzaldehyde, and p-n-octyloxybenzaldehyde. In view of adhesive property, p-n-octyloxybenzaldehyde is preferred.

Examples of the thiol compounds include 3-mercaptopropyltrimethoxysilane, 2-mercaptobenzooxazole, decanethiol, and thiobenzoic acid.

Examples of the sulfites include sodium sulfite, potassium sulfite, calcium sulfite, and ammonium sulfite.

Examples of the bisulfites include sodium bisulfite and potassium bisulfite.

Examples of the thiourea compounds include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

In view of the adhesive property and other properties of the dental composition obtained, the content of polymerization accelerator (F) in a dental composition of the present invention is preferably 0.01 mass % or more, more preferably 0.05 mass % or more, even more preferably 0.1 mass % or more, and is preferably 10 mass % or less, more preferably 7 mass % or less, even more preferably 5 mass % or less.

Organic Solvent (G)

Preferably, the dental composition of the present invention further comprises an organic solvent (G). With organic solvent (G), it is possible to improve adhesive property and coatability, and penetration into tooth structure, and prevent separation of the components in the dental composition.

Examples of the organic solvent (G) include methanol, ethanol, 1-propanol, 2-propanol, 1-butanol, 2-methyl-2-propanol, acetone, methyl ethyl ketone, tetrahydrofuran, diethyl ether, diisopropyl ether, hexane, toluene, chloroform, ethyl acetate, and butyl acetate. Considering biological safety and ease of removal by volatility, the organic solvent (G) is preferably a water-soluble organic solvent, specifically, ethanol, 2-propanol, 2-methyl-2-propanol, acetone, or tetrahydrofuran, more preferably ethanol, 2-propanol, 2-methyl-2-propanol, or tetrahydrofuran.

The content of organic solvent (G) in a dental composition of the present invention is preferably 1 mass % or more, more preferably 5 mass % or more, even more preferably 10 mass % or more, and is preferably 70 mass % or less, more preferably 50 mass % or less, even more preferably 30 mass % or less. In some embodiments, the organic solvent (G) may be absent.

Filler (H)

Preferably, the dental composition of the present invention further comprises a filler (H). The filler (H) can be broadly divided into organic filler, inorganic filler, and organic-inorganic composite filler. The filler (H) may be used alone, or two or more thereof may be used in combination. When two or more fillers are used in combination, the fillers may be fillers that differ in properties, for example, such as material, particle size distribution, and form. The filler (H) may be a commercially available product.

Examples of the material of the organic filler include polymethyl methacrylate, polyethyl methacrylate, a methyl methacrylate-ethyl methacrylate copolymer, crosslinked polymethyl methacrylate, crosslinked polyethyl methacrylate, polyamide, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. The organic filler may be used alone, or two or more thereof may be used in combination. The shape of the organic filler is not particularly limited.

Example of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass-ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. The inorganic filler may be used alone, or two or more thereof may be used in combination.

The shape of the inorganic filler is not particularly limited, and the inorganic filler may be, for example, irregular or spherical in shape. In view of improving the mechanical strength of the cured product, preferred for use as inorganic filler is a spherical filler. Here, the spherical filler may be a filler having an average uniformity of 0.6 or more as calculated for round-shaped particles observed in a unit field of a scanning electron micrograph (hereinafter, "SEM" for short) of the filler by dividing a particle diameter along a direction orthogonal to the maximum diameter by the maximum diameter. When using a spherical filler as inorganic filler, the average particle diameter is preferably 0.1 μm or more to maintain the mechanical strength of the cured product without decreasing the filling rate of the spherical filler in the dental composition. The average particle diameter is preferably 5 μm or less to provide a surface area sufficient to maintain the mechanical strength of the cured product.

In order to adjust the fluidity of the dental composition, the inorganic filler may be used after an optional surface treatment with a known surface treatment agent such as a silane coupling agent. Examples of such surface treatment agents include vinyltrimethoxysilane, vinyltriethoxysilane, vinyltrichlorosilane, vinyltri(β-methoxyethoxy)silane, γ-methacryloyloxypropyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler may be one prepared by pulverizing a product of polymerization of a paste-like material prepared by adding a monomer compound to the inorganic filler. Examples of the organic-inorganic composite filler include a TMPT filler (a polymerized and pulverized mixture of trimethylolpropanemethacrylate and a silica filler). The shape of the organic-inorganic composite filler is not particularly limited.

The particle diameter of filler (H) is not particularly limited, and the filler (H) may have an appropriately selected average particle diameter. In view of considerations such as handling of the product dental composition and the mechanical strength of the cured product, the average particle diameter of filler (H) is preferably 0.001 μm or more, and is preferably 50 μm or less, more preferably 10 μm or less. In this specification, the average particle diameter of filler (H) means the average particle diameter of primary particles of filler (H) (average primary particle diameter).

The average particle diameter of filler (H) can be determined by a laser diffraction scattering method or by electron microscopy of particles. Specifically, a laser diffraction scattering method is convenient for the measurement of particle sizes of 0.1 μm and more, whereas electron microscopy is more convenient for the measurement of ultrafine particles of less than 0.1 μm. Whether particles have a particle size of 0.1 μm or more can be determined by a laser diffraction scattering method.

For measurements using a laser diffraction scattering method, for example, a laser diffraction particle size distribution analyzer (SALD-2100, manufactured by Shimadzu Corporation) may be used with a 0.2% sodium hexametaphosphate aqueous solution used as dispersion medium.

In the case of electron microscopy, the average particle diameter can be determined by, for example, taking a micrograph with a scanning electron microscope (e.g., Model S-4000, manufactured by Hitachi), and measuring the size of particles (at least 200 particles) observed in a unit field of the micrograph, using image-analyzing particle-size-distribution measurement software (e.g., Macview, manufactured by Mountech Co., Ltd.). Here, the particle diameter of a particle is determined as the arithmetic mean value of the maximum and minimum lengths of the particle, and the average particle diameter is calculated from the number of particles and their particle diameters.

The content of filler (H) in a dental composition of the present invention is preferably 0.1 mass % or more, more preferably 0.5 mass % or more, even more preferably 1.0 mass % or more, and is preferably 30 mass % or less, more preferably 20 mass % or less, even more preferably 10 mass % or less.

Other Components

Aside from the foregoing components, a dental composition of the present invention may additionally comprise components such as a pH adjuster, a polymerization inhibitor, a fluorine ion-releasing component, an ultraviolet absorber, a thickener, a colorant, a fluorescent agent, a flavor, and an anti-microbial substance. Examples of the anti-microbial substance include cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, and triclosan.

The pH of a dental composition of the present invention is preferably 1.5 or more, more preferably 1.8 or more, even more preferably 2.0 or more, and is preferably 4.0 or less, more preferably 3.5 or less, even more preferably 3.0 or less. With the foregoing lower limits of pH, it is possible to effectively inhibit excessive demineralization in total etching—a process applied to tooth surface after etching with phosphoric acid—and improve adhesive property. With the foregoing upper limits of pH, the demineralization effect improves adhesive property in self-etching.

A preferred embodiment (Z-1) of a dental composition of the present invention is a dental composition that comprises a compound (A), a monomer (B) having an acidic group, water (C), a monomer (D) having no acidic group, and a polymerization initiator (E), in which the monomer (D) having no acidic group contains a hydrophobic monomer (D-1) having no acidic group and/or a hydrophilic monomer (D-2) having no acidic group, the polymerization initiator (E) is a photopolymerization initiator (E-1), and the content of water (C) is 5 to 30 mass %. Another preferred embodiment (Z-2) is a dental composition in which the total content of the all monomers contained in the dental composition of the embodiment (Z-1) is 20 to 90 mass %. Another preferred embodiment (Z-3) is a dental composition in which the content of the hydrophobic monomer (D-1) having no acidic group in the dental composition of the embodiment (Z-1) or (Z-2) is 15 to 80 mass % based on the mass of the all monomers contained in the dental composition. Another preferred embodiment (Z-4) is a dental composition in which the content of the hydrophilic monomer (D-2) having no acidic group in the dental composition of any of the embodiments (Z-1) to (Z-3) is 15 to 80 mass % based on the mass of the all monomers contained in the dental composition. Another preferred embodiment (Z-5) is a dental composition in which the content of the monomer (B) having an acidic group in the dental composition of any of the embodiments (Z-1) to (Z-4) is 3 to 30 mass % based on the mass of the all monomers contained in the dental composition. Another preferred embodiment (Z-6) is a dental composition in which the content of the compound (A) in the dental composition of any of the embodiments (Z-1) to (Z-5) is 1 to 30 mass %. In another preferred embodiment (Z-7), the dental composition of any of the embodiments (Z-1) to (Z-6) has a pH of 1.5 to 4.0. In all of the embodiments (Z-1) to (Z-7), the contents of the components may be appropriately varied following the foregoing descriptions, and addition, deletion, and other changes may be made to optional components such as polymerization accelerator (F).

A method of preparation of a dental composition of the present invention is not particularly limited, and a dental composition of the present invention can be obtained by mixing the components. The dental composition obtained may be charged into, for example, a single container to provide a one-part dental composition.

A dental composition of the present invention exhibits high adhesive property not only for tooth structure but for dental restoration materials such as metals, composite resins, and porcelain. This makes a dental composition of the present invention suited for use as an adhesive or a primer. The dental restoration material may be one having a fracture that has occurred in the mouth. A dental composition of the present invention is not particularly limited to specific methods of use, and may be used according to an ordinary method.

When used for bonding of a dental restoration material, a dental composition of the present invention may be used with, for example, a commercially available primer such as a primer for metal bonding, or with a dental surface cleaner such as hypochlorite or a hydrogen peroxide solution.

EXAMPLES

The following describes the present invention in greater detail by way of Examples. It should be noted, however, that the present invention is in no way limited by the following Examples. In the following, the following abbreviations are used.

Compound (A)
a1: 3-Methacryloyloxypropylmethyldimethoxysilane
a2: 3-Methacryloyloxypropylmethyldiethoxysilane
a3: 3-Methacryloyloxypropyldimethylmethoxysilane
Silane Coupling Agent Other Than Compound (A)
a'1: 3-Methacryloyloxypropyltrimethoxysilane
a'2: 3-Methacryloyloxypropyltriethoxysilane
a'3: 3-Methacryloyloxypropyltriisopropoxysilane
a'4: 8-Methacryloyloxyoctyltrimethoxysilane
a'5: 11-Methacryloyloxyundecanyltrimethoxysilane
Monomer (B) Having an Acidic Group
MDP: 10-Methacryloyloxydecyl dihydrogen phosphate
Hydrophobic Monomer (D-1) Having No Acidic Group
Bis-GMA: 2,2-Bis[4-(3-methacryloyloxy-2-hydroxypropoxy)phenyl]propane
Hydrophilic Monomer (D-2) Having No Acidic Group
HEMA: 2-Hydroxyethyl methacrylate
DEAA: N,N-Diethylacrylamide
Photopolymerization Initiator (E-1)
CQ: dl-Camphorquinone
BAPO: Bis(2,4,6-trimethylbenzoyl)phenylphosphine oxide
Polymerization Accelerator (F)
DABE: Ethyl 4-(N,N-dimethylamino)benzoate
DEPT: N,N-Bis(2-hydroxyethyl)-p-toluidine
Filler (H)

Silica: Fine particle silica, Aerosil R-972, manufactured by Nippon Aerosil Co., Ltd.; average particle diameter: 16 nm
Other Components
BHT: 2,6-Di-t-butyl-4-methylphenol (stabilizer and polymerization inhibitor)

Examples 1 to 12 and Comparative Examples 1 to 9

One-part dental compositions were prepared by mixing the components in the amounts shown in Tables 1 and 2. The dental compositions were each measured for tensile bond strength against dental porcelain, enamel, and dentin, using the methods described below. The dental compositions were also measured for pH. The results are presented in Tables 1 and 2. For evaluation of storage stability of the dental compositions, the tensile bond strength of dental composition was measured after a 7-day storage period at 4° C. (after 7 days from preparation). For the measurement of tensile bond strength against dental porcelain, the dental composition was also measured immediately after preparation (within 15 minutes of preparation). The pH of the dental composition was measured immediately after preparation (within 15 minutes of preparation), using a pH meter equipped with glass electrodes and that uses a potassium chloride solution (a compact pH meter LAQUAtwin, manufactured by Horiba Ltd.).

Tensile Bond Strength Measurement Against Dental Porcelain

A dental porcelain (VITABLOCS Mark II, a feldspathic ceramic) was ground with #1000 silicon carbide paper under running water. After grinding, the ceramic was dried by blowing away water from surface with air. An adhesive tape, about 150 μm thick, having a round hole of 5 mm diameter was attached to the dry, smooth surface to define the bonding area.

The dental composition fabricated in each Example or Comparative Example was applied to the ceramic through the round hole with a brush, and, after 3 seconds, the surface was dried by blowing air until the applied dental composition lost fluidity. The dental composition was then cured by applying light for 10 seconds with a dental visible-light irradiator (manufactured by J. Morita Corp. under the trade name PenCure 2000).

A dental filling composite resin (manufactured by Kuraray Noritake Dental Inc. under the trade name Clearfil® AP-X) was used to fill the surface of the cured dental composition, and a release film (polyester) was placed over the resin. With a glass slide mounted on the release film, the surface of the applied dental filling composite resin was leveled by pressing the glass slide. The dental filling composite resin was cured by applying light for 20 seconds via the release film, using the dental visible-light irradiator.

A cylindrical stainless steel rod (measuring 7 mm in diameter and 2.5 cm in length) was bonded at its one end face (circular end face) to the surface of the cured dental filling composite resin, using a commercially available dental resin cement (manufactured by Kuraray Noritake Dental Inc. under the trade name PANAVIA® 21). The sample was allowed to stand at room temperature for 30 minutes, and immersed in distilled water to obtain a bonding test sample. Here, a total of twenty bonding test samples was fabricated, and each sample was allowed to stand for 24 hours in a thermostatic chamber at a maintained temperature of 37° C. In order to evaluate the initial bond strength, ten of the twenty samples were measured for tensile bond strength (initial bonding) immediately after the 24-hour storage period. For evaluation of bond durability, the other ten samples were measured for tensile bond strength after being alternately immersed for 1 minute in 4° C. cold water and in 60° C. hot water in a thermal cycle repeated 10,000 times (bond durability).

The tensile bond strength of the bonding test sample was measured using a universal testing machine (Autograph AG-I, 100 kN, manufactured by Shimadzu Corporation) with a crosshead speed set at 2 mm/minute. The readings were averaged to find the tensile bond strength of the bonding test sample.

Tensile Bond Strength Measurement Against Enamel or Dentin

The labial surfaces of bovine mandibular incisors were ground with #80 silicon carbide paper (manufactured by Nihon Kenshi Co., Ltd.) under running water to obtain samples with exposed flat enamel surfaces and samples with exposed flat dentin surfaces. Each sample was further ground with #1000 silicon carbide paper (manufactured by Nihon Kenshi Co., Ltd.) under running water. After grinding, the tooth was dried by blowing away water from tooth surface with air. An adhesive tape, about 150 μm thick, having a round hole of 3 mm diameter was attached to the dry, smooth surface to define the bonding area.

The dental composition fabricated in each Example or Comparative Example was applied to the surface through the round hole with a brush, and, after 3 seconds, the surface was dried by blowing air until the applied dental composition lost fluidity. The dental composition was then cured by applying light for 10 seconds with a dental visible-light irradiator (manufactured by J. Morita Corp. under the trade name PenCure 2000).

A dental filling composite resin (manufactured by Kuraray Noritake Dental Inc. under the trade name Clearfil® AP-X) was used to fill the surface of the cured dental composition, and a release film (polyester) was placed over the resin. With a glass slide mounted on the release film, the surface of the applied dental filling composite resin was leveled by pressing the glass slide. The dental filling composite resin was cured by applying light for 20 seconds via the release film, using the dental visible-light irradiator.

A cylindrical stainless steel rod (measuring 7 mm in diameter and 2.5 cm in length) was bonded at its one end face (circular end face) to the surface of the cured dental filling composite resin, using a commercially available dental resin cement (manufactured by Kuraray Noritake Dental Inc. under the trade name PANAVIA® 21). The sample was allowed to stand at room temperature for 30 minutes, and immersed in distilled water to obtain a bonding test sample. Here, a total of twenty bonding test samples was fabricated, and each sample was allowed to stand for 24 hours in a thermostatic chamber at a maintained temperature of 37° C. In order to evaluate the initial bond strength, ten of the twenty samples were measured for tensile bond strength (initial bonding) immediately after the 24-hour storage period. For evaluation of bond durability, the other ten samples were measured for tensile bond strength after being alternately immersed for 1 minute in 4° C. cold water and in 60° C. hot water in a thermal cycle that was repeated 4,000 times (bond durability).

The tensile bond strength of the bonding test sample was measured using a universal testing machine (Autograph AG-I, 100 kN, manufactured by Shimadzu Corporation) with a crosshead speed set at 2 mm/minute. The readings were averaged to find the tensile bond strength of the bonding test sample.

TABLE 1

| Components (mass %) | | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|---|
| Compound (A) | a1 | 4.3 | | | | | | | | | | | |
| | a2 | | 0.9 | 2.6 | 4.3 | 5.9 | 8.2 | 11.9 | 15.2 | | 4.3 | 4.3 | 4.3 |
| | a3 | | | | | | | | | 4.3 | | | |
| Silane coupling agent other than compound (A) | a'1 | | | | | | | | | | | | |
| | a'2 | | | | | | | | | | | | |
| | a'3 | | | | | | | | | | | | |
| | a'4 | | | | | | | | | | | | |
| | a'5 | | | | | | | | | | | | |
| Monomer (B) having acidic group | MDP | 8.6 | 8.9 | 8.7 | 8.6 | 8.4 | 8.2 | 7.9 | 7.6 | 8.6 | 8.6 | 8.6 | 8.6 |
| Water (C) | | 12.9 | 13.3 | 13.1 | 12.9 | 12.7 | 12.3 | 11.9 | 11.4 | 12.9 | 4.3 | 8.6 | 17.2 |
| Hydrophobic monomer (D-1) having no acidic group | Bis-GMA | 30.06 | 31.06 | 30.56 | 30.06 | 29.66 | 28.96 | 27.46 | 26.56 | 30.06 | 30.06 | 30.06 | 30.06 |
| Hydrophilic monomer (D-2) having no acidic group | HEMA | 10.7 | 11.1 | 10.9 | 10.7 | 10.5 | 10.3 | 9.9 | 9.5 | 10.7 | 10.7 | 10.7 | 10.7 |
| | DEAA | 10.7 | 11.1 | 10.9 | 10.7 | 10.5 | 10.3 | 9.9 | 9.5 | 10.7 | 10.7 | 10.7 | 10.7 |
| Photopolymerization initiator (E-1) | CQ | 1.7 | 1.8 | 1.7 | 1.7 | 1.7 | 1.6 | 1.6 | 1.5 | 1.7 | 1.7 | 1.7 | 1.7 |
| | BAPO | 0.6 | 0.7 | 0.7 | 0.6 | 0.6 | 0.6 | 0.6 | 0.6 | 0.6 | 0.6 | 0.6 | 0.6 |
| Polymerization accelerator (F) | DABE | 0.9 | 0.9 | 0.9 | 0.9 | 0.8 | 0.8 | 0.8 | 0.8 | 0.9 | 0.9 | 0.9 | 0.9 |
| | DEPT | 0.6 | 0.7 | 0.7 | 0.6 | 0.6 | 0.6 | 0.6 | 0.6 | 0.6 | 0.6 | 0.6 | 0.6 |
| Solvent (G) | Ethanol | 12.9 | 13.3 | 13.1 | 12.9 | 12.7 | 12.3 | 11.9 | 11.4 | 12.9 | 21.5 | 17.2 | 8.6 |
| Filler (H) | Silica | 6.0 | 6.2 | 6.1 | 6.0 | 5.9 | 5.8 | 5.5 | 5.3 | 6.0 | 6.0 | 6.0 | 6.0 |
| Other components | BHT | 0.04 | 0.04 | 0.04 | 0.04 | 0.04 | 0.04 | 0.04 | 0.04 | 0.04 | 0.04 | 0.04 | 0.04 |

TABLE 2

| Components (mass %) | | Comp. Ex. 1 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 |
|---|---|---|---|---|---|---|---|---|---|---|
| Compound (A) | a1 | | | | | | | | | |
|  | a2 | | | | | | | 4.3 | 4.3 | 4.3 |
|  | a3 | | | | | | | | | |
| Silane coupling | a'1 | 4.3 | | | | | | | | |
| agent other than | a'2 | | 4.3 | | | | | | | |
| compound (A) | a'3 | | | 4.3 | | | | | | |
|  | a'4 | | | | 4.3 | | | | | |
|  | a'5 | | | | | 4.3 | | | | |
| Monomer (B) having acidic group | MDP | 8.6 | 8.6 | 8.6 | 8.6 | 8.6 | 9.0 | | 8.6 | 8.6 |
| Water (C) | | 12.9 | 12.9 | 12.9 | 12.9 | 12.9 | 13.4 | 12.9 | 0.4 | |
| Hydrophobic monomer (D-1) having no acidic group | Bis-GMA | 30.06 | 31.06 | 30.56 | 30.06 | 29.66 | 28.96 | 27.46 | 26.56 | 30.06 |
| Hydrophilic monomer | HEMA | 10.7 | 10.7 | 10.7 | 10.7 | 10.7 | 11.2 | 12.9 | 10.7 | 10.7 |
| (D-2) having no acidic group | DEAA | 10.7 | 10.7 | 10.7 | 10.7 | 10.7 | 11.3 | 12.9 | 10.7 | 10.7 |
| Photopolymerization | CQ | 1.7 | 1.7 | 1.7 | 1.7 | 1.7 | 1.8 | 1.7 | 1.7 | 1.7 |
| initiator (E-1) | BAPO | 0.6 | 0.6 | 0.6 | 0.6 | 0.6 | 0.7 | 0.6 | 0.6 | 0.6 |
| Polymerization | DABE | 0.9 | 0.9 | 0.9 | 0.9 | 0.9 | 0.9 | 0.9 | 0.9 | 0.9 |
| accelerator (F) | DEPT | 0.6 | 0.6 | 0.6 | 0.6 | 0.6 | 0.7 | 0.6 | 0.6 | 0.6 |
| Solvent (G) | Ethanol | 12.9 | 12.9 | 12.9 | 12.9 | 12.9 | 13.4 | 12.9 | 25.3 | 25.7 |
| Filler (H) | Silica | 6.0 | 6.0 | 6.0 | 6.0 | 6.0 | 6.3 | 6.0 | 6.0 | 6.0 |
| Other components | BHT | 0.04 | 0.04 | 0.04 | 0.04 | 0.04 | 0.04 | 0.04 | 0.04 | 0.04 |

The invention claimed is:

1. A one-part dental composition comprising a compound (A) represented by the following general formula (1), a monomer (B) having an acidic group, and water (C),

$$Y\text{—}SiR_nX_{(3-n)} \qquad (1),$$

wherein Y represents a monovalent organic group having a polymerizable group that is a (meth)acryloyl group, R represents a group selected from the group consisting of an alkyl group, an aryl group, and an aralkyl group, X represents a hydroxyl group or a hydrolyzable group, and n represents an integer of 1 or 2, in which the plurality of R may be the same or different, and the plurality of X may be the same or different, and the content of the water (C) is 1.0 to 50 mass %.

2. The dental composition according to claim 1, wherein the dental composition comprises the compound (A) in an amount of 0.1 to 50 mass %.

3. The dental composition according to claim 1, wherein the monomer (B) having an acidic group is a monomer having a phosphoric acid group.

4. The dental composition according to claim 1, further comprising a monomer (D) having no acidic group.

5. The dental composition according to claim 1, wherein the total content of all monomers contained in the dental composition is 20 to 90 mass %.

6. The dental composition according to claim 1, wherein the content of the monomer (B) having an acidic group is 1 to 50 mass % relative to all monomers contained in the dental composition.

7. The dental composition according to claim 1, further comprising a polymerization initiator (E).

8. The dental composition according to claim 7, wherein the polymerization initiator (E) is a photopolymerization initiator (E-1).

9. The dental composition according to claim 1, wherein the dental composition has a pH of 1.5 to 4.0.

10. The dental composition according to claim 1, wherein the dental composition is packed in a container.

11. An adhesive comprising the dental composition of claim 1.

12. A primer comprising the dental composition of claim 1.

* * * * *